US012806326B2

(12) United States Patent
Connolly

(10) Patent No.: US 12,806,326 B2
(45) Date of Patent: Nov. 24, 2026

(54) RESPIRATORY AIRWAY EVACUATION DEVICE

(71) Applicant: Maine Health Center, Portland, ME (US)

(72) Inventor: William Connolly, South Portland, ME (US)

(73) Assignee: Maine Medical Center, Portland, ME (US)

( * ) Notice: Subject to any disclaimer, the term of this patent is extended or adjusted under 35 U.S.C. 154(b) by 694 days.

(21) Appl. No.: 18/203,538

(22) Filed: May 30, 2023

(65) Prior Publication Data

US 2023/0381396 A1 Nov. 30, 2023

Related U.S. Application Data

(60) Provisional application No. 63/347,185, filed on May 31, 2022.

(51) Int. Cl.

*A61M 1/00* (2006.01)
*A61B 90/40* (2016.01)

(52) U.S. Cl.

CPC ............... *A61M 1/71* (2021.05); *A61B 90/40* (2016.02); *A61B 2090/401* (2016.02)

(58) Field of Classification Search

CPC ........... A61B 17/24; A61M 1/71; A61M 1/76; A61M 1/77; A61M 1/84; A61M 1/85; A61M 1/86; A61M 1/87; A61M 1/815
USPC .... 606/106, 160, 161, 162; 604/167.04, 533
See application file for complete search history.

(56) References Cited

U.S. PATENT DOCUMENTS 6,257,626 B1 * 7/2001 Campau .............. F16L 37/0985 285/423
2005/0192543 A1 * 9/2005 Sibbitt ................ A61M 5/3148 604/218
2013/0090665 A1 * 4/2013 Linde ...................... A61M 1/84 606/106

* cited by examiner

*Primary Examiner* — Tuan V Nguyen
(74) *Attorney, Agent, or Firm* — Armis IP Law, LLC

(57) ABSTRACT

In a trauma, emergency room/department (ER/ED) or similar exigent treatment environment, an emergency airway evacuation device includes a vacuum body adapted for receiving a suctioned volume, and an actuator engaged with the vacuum body for inducing a lowered pressure therein for suctioned removal of airway blockage matter. An elongated extraction tube is fluidically coupled to the vacuum body for transporting the suctioned volume from a respiratory blockage region, and includes a curved, tapered tip for insertion into the blockage region. The device is small and portable for use as an "on person" accessory suitable in cost and size for widespread distribution to medical treatment providers.

16 Claims, 4 Drawing Sheets

RESPIRATORY AIRWAY EVACUATION DEVICE

RELATED APPLICATIONS

This patent application claims the benefit under 35 U.S.C. § 119(e) of U.S. Provisional Patent App. No. 63/347,187, filed May 31, 2022, entitled "RESPIRATORY AIRWAY EVACUATION DEVICE," incorporated herein by reference in entirety.

BACKGROUND

Establishment and continuity of a respiratory airway is significant in both Basic Life Support, and Advanced Cardiac Life support. Medical treatment bays often have wall suction which can facilitate treatment of airway compromise, and mobile equipment may be transported to a treatment location. However, any environment where a compromised airway is possible and does not have immediate access to sophisticated suction systems may present a challenge for airway remediation, and such compromise can be quite common in emergency treatment environments, particularly for substance overdose cases.

SUMMARY

In a trauma, emergency room/department (ER/ED) or similar exigent treatment environment, an emergency airway evacuation device includes a vacuum body adapted for receiving a suctioned volume, and an actuator engaged with the vacuum body for inducing a lowered pressure therein for suctioned removal of airway blockage matter. An elongated extraction tube is fluidically coupled to the vacuum body for transporting the suctioned volume from a respiratory blockage region, and includes a curved, tapered tip for insertion into the blockage region. The device is small and portable for use as an "on person" accessory suitable in cost and size for widespread distribution to medical treatment providers.

Configurations herein are based, in part, on the observation that airway obstruction, such as by disgorged or expelled gastric/stomach content, presents an exigent, life threatening situation. Airway obstruction and consequential lack of respiration and blood oxygenation can prove fatal or permanently debilitating within minutes. Unfortunately, conventional approaches to emergency lifesaving measures suffer from the shortcoming that they often require patent transport to a machine or treatment room. Mechanical suction, such as from accessible wall ports, is typically installed in patient rooms and require transport and connection of suction apparatus in order to be effective.

Accordingly, configurations herein substantially overcome the shortcomings of conventional medical devices by providing a small, portable suction and manipulation device for immediate evacuation of a patient airway to restore natural breathing. The disclosed device is small enough to be carried as personal equipment, in a pocket or utility pouch, and allows immediate response to a patient airway obstruction by suctioning out any liquidus or semi-solid material obstructing the airway.

In further detail, the configurations herein depict an emergency airway evacuation device having a vacuum body adapted for receiving a suctioned volume, and an actuator engaged with the vacuum body for inducing a lowered pressure therein. The vacuum body is adapted for engagement with an elongated extraction tube fluidically coupled to the vacuum body for transporting the suctioned volume from a respiratory trauma region.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Depicted below are several examples of the evacuation device; other and alternate configurations may be apparent without deviating from the core concept.

In a medical treatment facility, robust treatment bays and wheeled devices can provide sophisticated airway evacuation treatment for a resident patient, however usage in exigent situations such as during transport and emergency on-site response are not feasible for timely intervention if equipment is not immediately available. Airway compromise presents a narrow timeframe for effective treatment. The evacuation device as disclosed herein provides a small, manually powered device which may be carried by medical personnel and quickly deployed for removal of blockage material sufficient to reestablish the airway and stabilize the patient until transport to a more comprehensive treatment setting.

Figure 1:
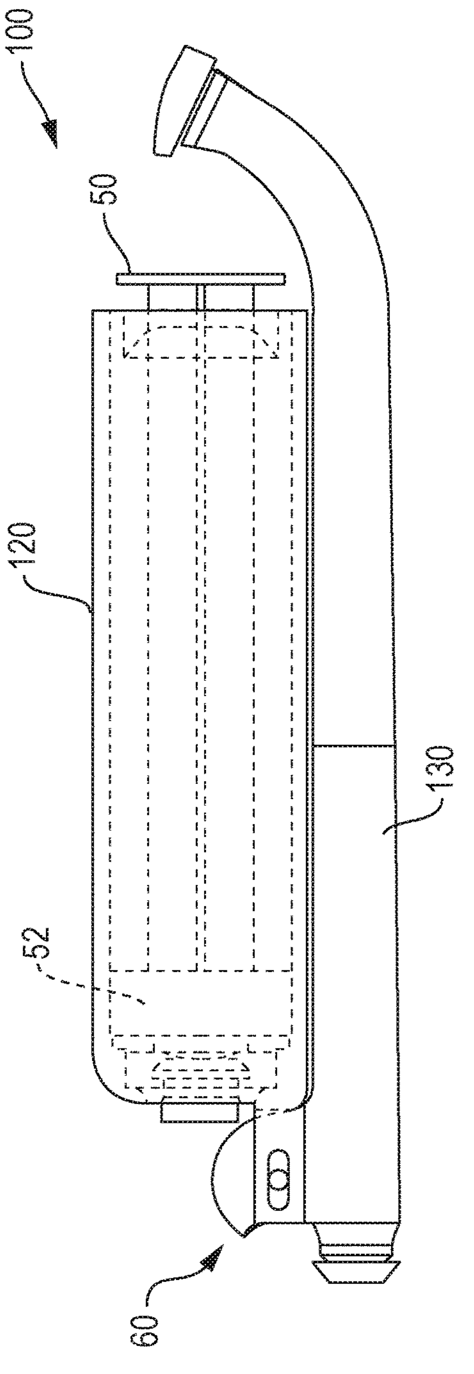
FIG. 1 shows a perspective view of the emergency airway evacuation device in an undeployed, or folded position for easy storage.
Figure 2:
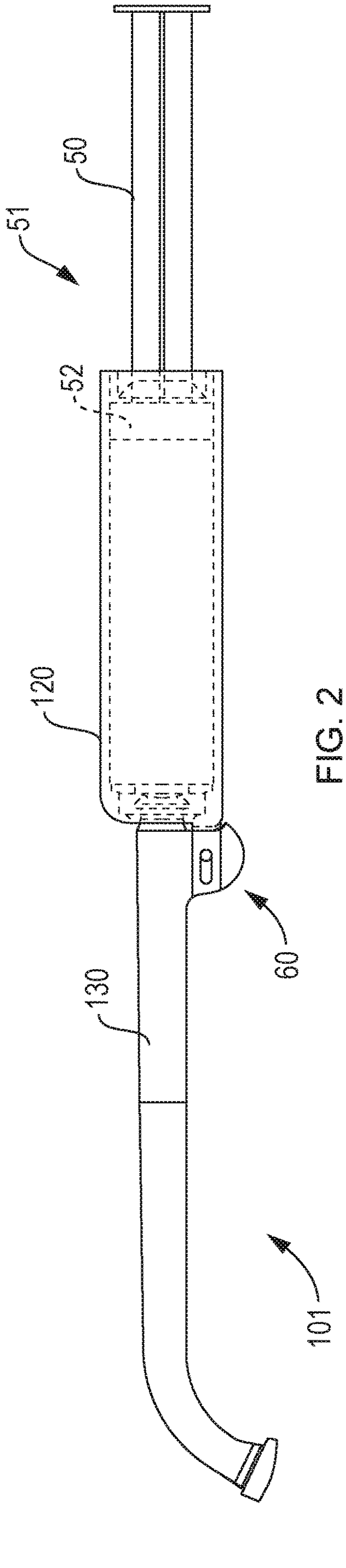
FIG. 2 shows a perspective view of the device of FIG. 1 in a deployed position.

FIG. 1 shows a perspective view of the emergency airway evacuation device in an undeployed, or folded position for easy storage. FIG. 2 shows a perspective view of the device of FIG. 1 in a deployed 101 position. Referring to FIGS. 1 and 2, the evacuation device includes a vacuum body 120 adapted for generation of low pressure or suction from an actuator 50 slidably engaged with an interior of the vacuum body 120. The actuator is disposed for drawing a plunger 52 in sealing engagement with the interior for inducing a reduced pressure in the vacuum body through displacement of the plunger 52 through a volume in the vacuum body.

In the example arrangement, the vacuum body 120 includes cylindrical walls and the plunger has a diameter corresponding to the cylindrical walls, where the plunger is formed from a resilient material for defining the sealing engagement with the interior of the vacuum, similar to a syringe for providing immediate, on-site suction for removal of fluids or expelled contents from a distressed patient. A hinge 60, discussed further below, rotates an extraction tube

130 for engagement with the vacuum body 120 for suctioning airway obstructive matter by withdrawing the actuator to generate suction, also shown in further detail below.

Figure 3A:
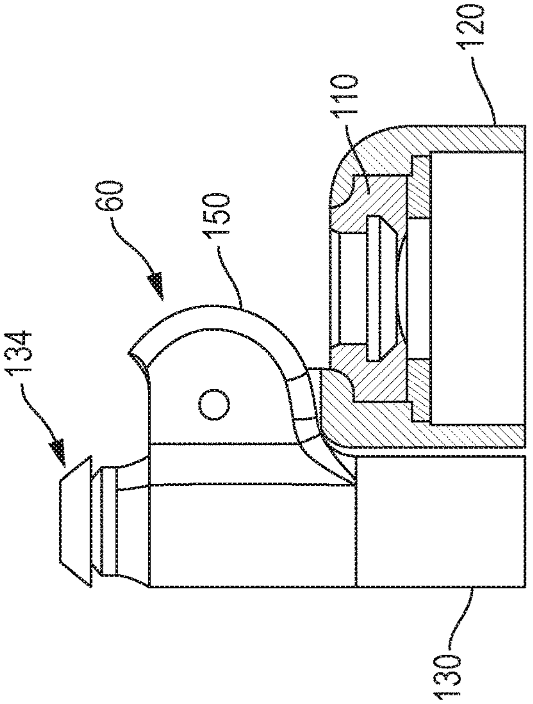
FIGS. 3A and 3B show a side cutaway view of the hinge of FIGS. 1 and 2 in a respective undeployed and deployed position.
Figure 3B:
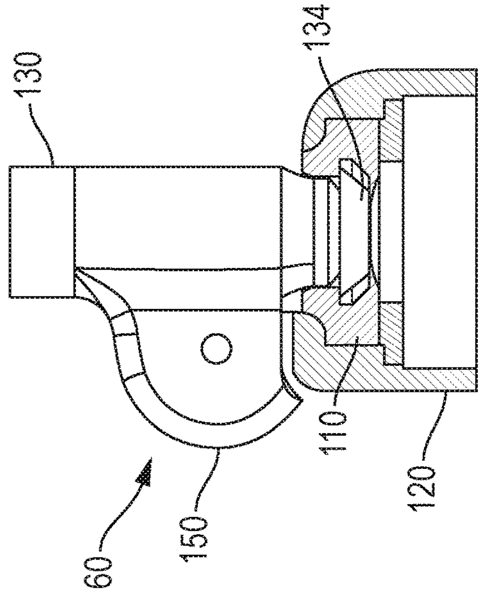

FIGS. 3A and 3B show a side cutaway view of the hinge of FIGS. 1 and 2 in a respective undeployed and deployed 101 position. Referring to FIGS. 1-3B, to aid in portability and allow for compact transport in a pocket or kit, the evacuation device employs the hinge 60 disposed between the extraction tube 130 and the vacuum body 120. The hinge 60 is configured for disposing the extraction tube 130 between an undeployed position that extends the extraction tube parallel to the vacuum body in a folded position, and the deployed 101 position that engages the extraction tube in fluidic communication with the vacuum body 120. The deployed position allows the extraction tube to frictionally and/or slidably engage a tubular tip of the vacuum body by "sliding over" the tip based on a slightly larger diameter of the extraction tube. Thus, the extraction tube includes a proximate end adapted to engage the vacuum body, and a distal end having a curved, tapered tip for insertion into the respiratory trauma region.

Figure 4A:
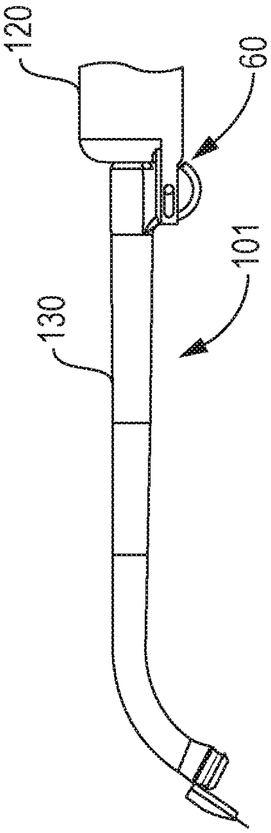
FIGS. 4A and 4B show side elevation views of the device of FIGS. 1-3B in deployed and undeployed positions.
Figure 4B:
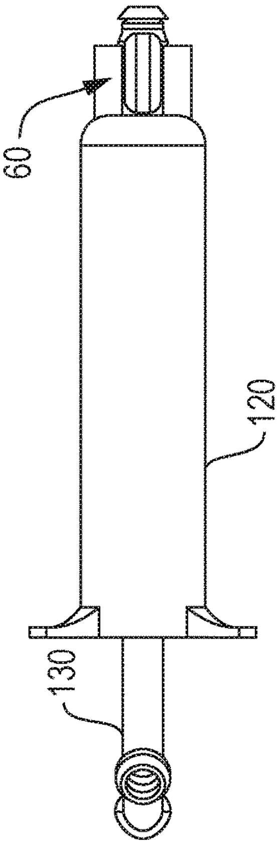
Figure 5A:
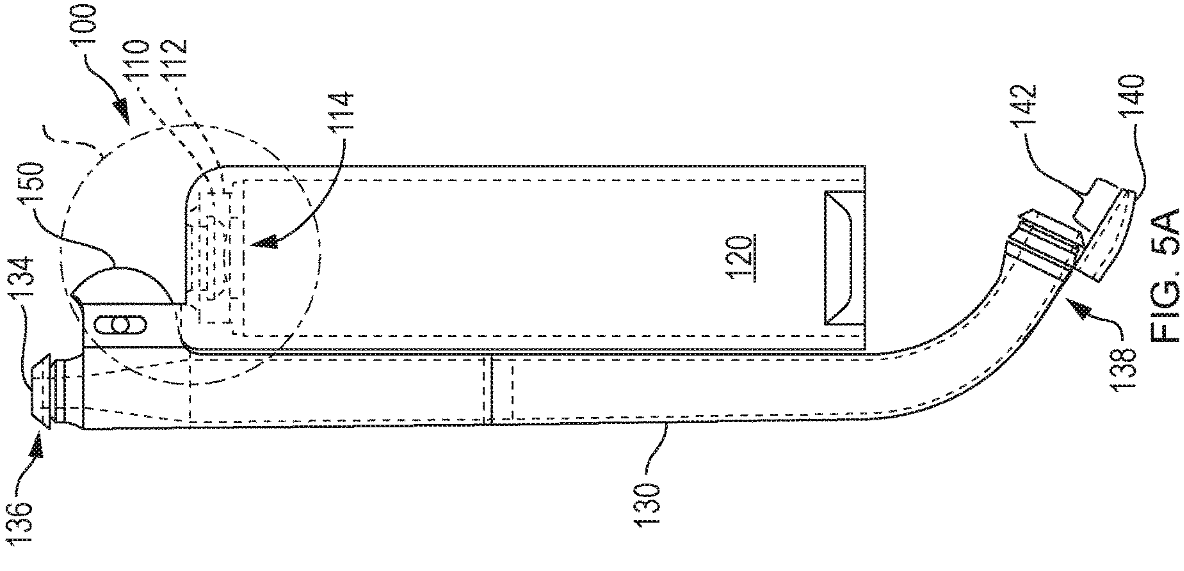
FIGS. 5A-5C show cutaway views of the vacuum body and extraction tube of FIGS. 1-4B in an undeployed position.
Figure 5B:
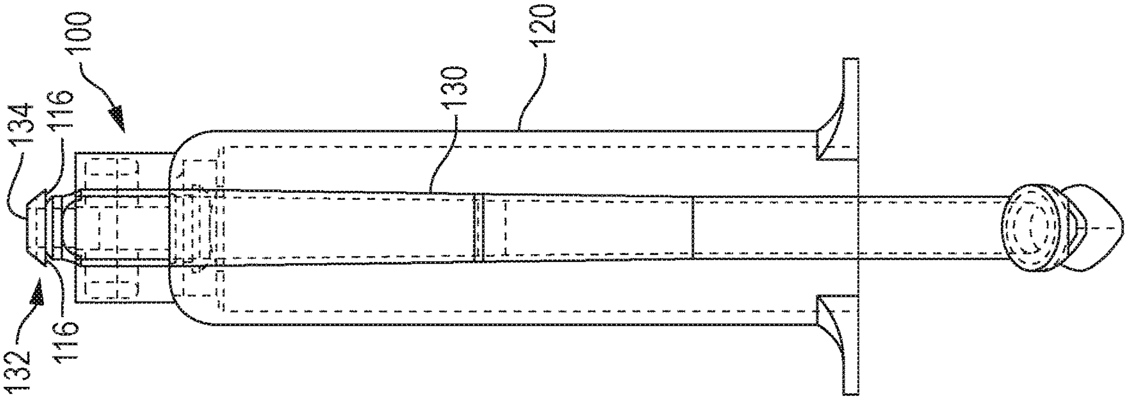
Figure 5C:
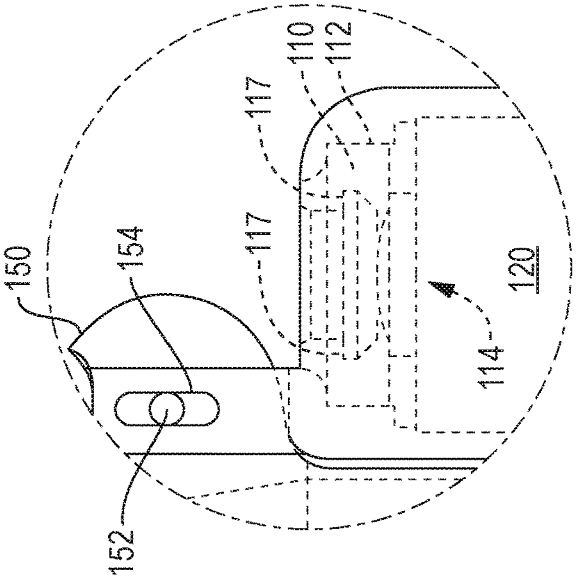
Figure 6C:
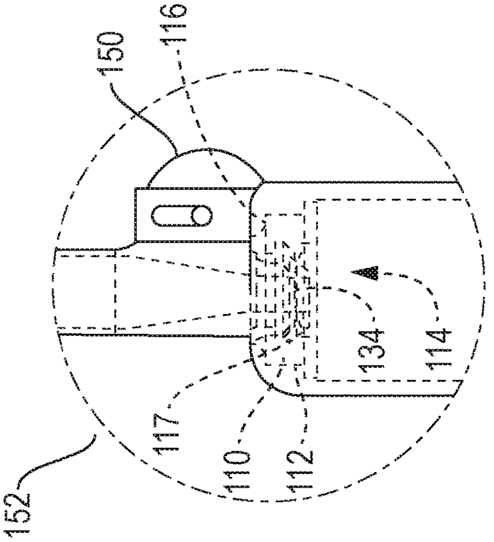
FIGS. 6A-6C show cutaway views of the vacuum body and extraction tube of FIGS. 1-4B in a deployed position.
Figure 6B:
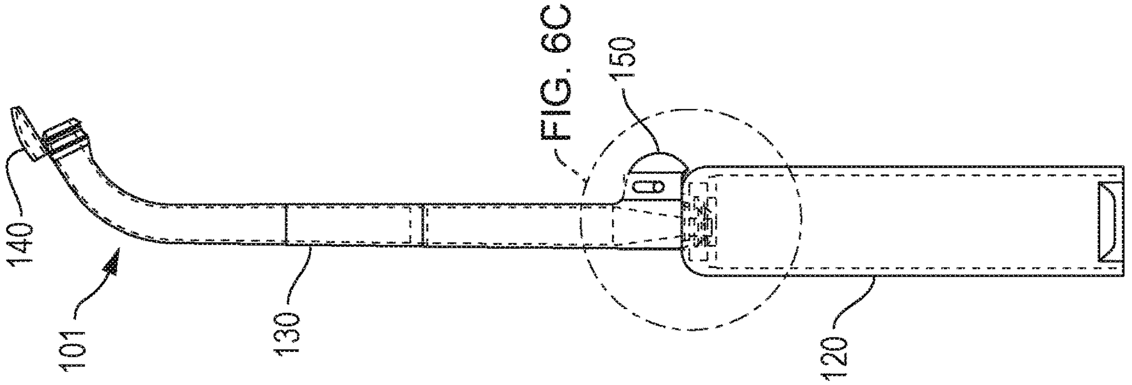
Figure 6A:
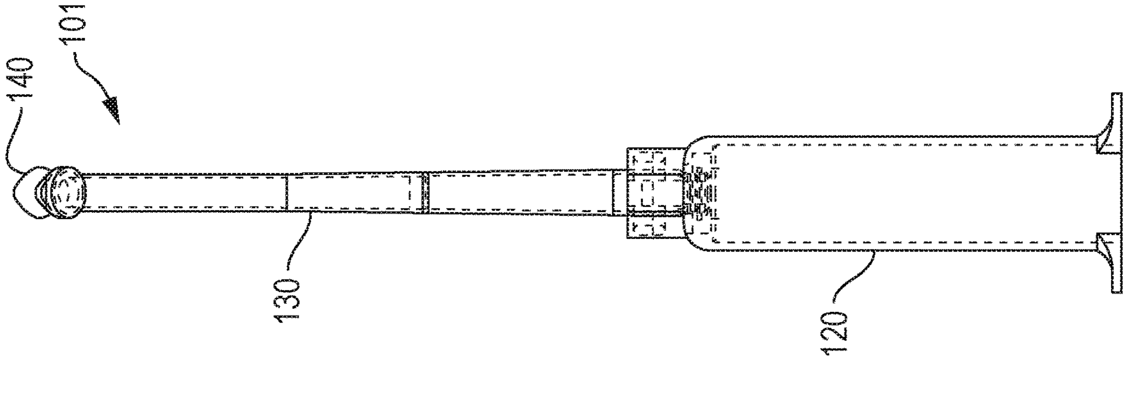

FIGS. 4A and 4B show side elevation views of the device of FIGS. 1-3B in deployed and undeployed positions. Referring to FIGS. 4A and 4B, in FIG. 4A, the deployed device has a length extending from the vacuum body 120, similar to a barrel of a syringe. A folded position in FIG. 4B shows that the hinge 60 allows the extraction tube to invert 180 degrees parallel to the vacuum body 120 for compact storage. FIGS. 5A-5C show cutaway views of the vacuum body and extraction tube of FIGS. 1-4B in an undeployed position, and FIGS. 6A-6C show cutaway views of the vacuum body and extraction tube of FIGS. 1-4B in a deployed position. Referring to FIGS. 1-6C, the hinge 60 may take a variety of forms from a resilient polymer and/or flexible construction. In the example configuration shown herein, the hinge 60 includes a protrusion and a pivot base including posts, such that the protrusion is flanked by the posts. A pivotal junction rotationally couples the protrusion to the flanking posts, by a dimple, axle or frictional engagement, to allow the evacuation tube to rotationally pivot or "swing" about 180 degrees to align and engage the tip on the vacuum body and provide a consistent fluidic connection.

Operation includes insertion of the evacuation tube 130 into the blockage region, typically the mouth, throat and esophageal regions, and withdrawing the actuator 50 to suction blockage material into the vacuum body 120. Repeated iterations may be performed by expelling the withdrawn contents through reverse actuation movement to free the vacuum body for successive operation.

In a particular prototype, illustrated below, the inverted portable suction device 100 achieves a deployed position 101 through a resilient engagement of an annular bushing 110 disposed in a groove 112 at an exit or suction orifice 114 of the vacuum body 120. A tapered collar 134 at a proximate end 136 of the extraction tube 130 has a sloped or tapered diameter 132 for deformable engagement with the annular bushing 110. The tapered collar includes a flat lip 116 such that the annular bushing 110 compressively engages the flat lip 116 for locking the tapered collar 134 against the annular bushing 110. The annular bushing 110 is formed from a deformable material to slidably compress against the tapered diameter 132 during insertion until an insertion depth sufficient to permit the sloped diameter to surpass the flat lip 116 and engage a ridge 117 of the annular bushing 110, shown in FIG. 5C as a magnification of circled region "A" of FIG. 5A. At the insertion depth, the flat lip 116 engages the complementary flat ridge 117 surface on the annular bushing for enforcing a single use locking attachment. Once engaged, the flat lip 116 is prevented from withdrawal against the flat ridge, thereby ensuring that the device cannot be refolded and reused after possible contamination from gastric contents.

This achieves a permanent or semi-permanent engagement for providing a fluidic seal and enforcement of a single usage, as the evacuated material may be of unknown origin and constitute a hazardous material and/or biohazard.

The extraction tube 130 has a proximate end 136 and a distal end 138, such that the proximate end 136 is adapted to engage a suction orifice 114 responsive to reduced pressure in the vacuum body 120. The distal end 138 is adapted for fluidic communication with the respiratory trauma region, generally the oral cavity and throat region of the afflicted patient where the harmful emesis material resides. Since the emesis material for evacuation has an unknown origin and may be of various texture and viscosity, a rake 140 is defined by a surface adjacent the distal end 138, where the surface has an area 142 adapted for manual manipulation of viscous or solid material for aiding suction or simply direct removal or "shoveling" of particulate matter. As the device is intended as an exigent treatment pending more robust care, evacuated material may be transferred to any nearby sacrificial textile surface such as the patient's or caretaker's clothing.

The rake 140 has a deformability for nonabrasive contact with tissue and a resiliency for manipulation of solids and semi-solids. This pliable, resilient texture may be provided by silicon or similar rubber and/or polymer construction. The rake 140 defines an annular surface based on a circumference of the extraction tube 130, and may follow a portion of the extraction tube circumference, such that the annular surface increases a rigidity of the rake surface.

The vacuum body 120 has a volume based on a volume of a patient oral cavity, and may undergo multiple extractions to evacuate all material. Suction may be provided by a suitable diaphragm and/or plunger arrangement for inducing low pressure, such as by a modified syringe.

Engagement of the extraction tube 130 with the vacuum body 120 may involve a cam 150 attached at the proximate end 136 of the extraction tube, where the cam 150 attaches with pins 152 in a slot 154 for providing rotational movement of the extraction tube to alignment in a parallel position with the vacuum body, and then linear movement for engaging the extraction tube 130 with the vacuum body 120 by manually pushing the extraction tube 130 towards the vacuum body 120 to slidably force the tapered diameter 132 against the annular bushing 110 past the flat lip 116.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. An emergency airway evacuation device, comprising a vacuum body adapted for receiving a suctioned volume;

an actuator engaged with the vacuum body for inducing a lowered pressure in the vacuum body;

an elongated extraction tube, the extraction tube fluidically coupled to the vacuum body for transporting the suctioned volume from a respiratory trauma region; and a hinge, the hinge disposed between the extraction tube and the vacuum body, the hinge configured for disposing the extraction tube between an undeployed position that extends the extraction tube parallel to the vacuum body, and a deployed position that engages the extraction tube in fluidic communication with the vacuum body.

2. The device of claim 1 wherein the actuator is slidably engaged with an interior of the vacuum body, the actuator disposed for drawing a plunger in sealing engagement with the interior for inducing a reduced pressure in the vacuum body resulting from volume displacement in the vacuum body.

3. The device of claim 2 wherein the vacuum body includes cylindrical walls and the plunger has a diameter corresponding to the cylindrical walls, the plunger formed from a resilient material for defining the sealing engagement with the interior of the vacuum body.

4. The device of claim 1 where the extraction tube includes a proximate end adapted to engage the vacuum body, and a distal end having a curved, tapered tip for insertion into the respiratory trauma region.

5. The device of claim 1 wherein the hinge includes:
a protrusion and a pivot base including posts,
the protrusion flanked by the posts; and
a pivotal junction rotationally coupling the protrusion to the flanking posts.

6. The device of claim 1, further comprising:
a resilient engagement, the resilient engagement securing the vacuum body to the extraction tube for engagement with the vacuum body.

7. The device of claim 6 wherein the resilient engagement includes an annular bushing disposed in a groove at an exit orifice of the vacuum body.

8. The device of claim 7 further comprising a tapered collar at a proximate end of the extraction tube, the tapered collar having a sloped diameter for deformable engagement with the annular bushing.

9. The device of claim 8 wherein the tapered collar includes a flat lip, the annular bushing compressively engaging the flat lip for locking the tapered collar against the annular bushing.

10. The device of claim 9 wherein the flat lip engages a complementary flat surface on the annular bushing for enforcing a single use locking attachment.

11. The device of claim 1 wherein the extraction tube has a proximate end and a distal end, the proximate end adapted to engage a suction orifice responsive to reduced pressure in the vacuum body, and a distal end adapted for fluidic communication with the respiratory trauma region.

12. The device of claim 11 further comprising a rake defined by a surface adjacent the distal end, the surface having an area adapted for manual manipulation of viscous or solid material.

13. The device of claim 12 wherein the rake has a deformability for nonabrasive contact with tissue and a resiliency for manipulation of solids and semi-solids.

14. The device of claim 1 wherein the vacuum body has a volume based on a volume of a patient oral cavity.

15. The device of claim 1 further comprising a cam attached at a proximate end of the extraction tube, the cam coupled with pins in a slot for providing rotational movement of the extraction tube to a parallel position with the vacuum body, and linear movement for engaging the extraction tube with the vacuum body.

16. An emergency airway evacuation device, comprising
a vacuum body adapted for receiving a suctioned volume;
an actuator engaged with the vacuum body for inducing a lowered pressure in the vacuum body;
an elongated extraction tube, the extraction tube fluidically coupled to the vacuum body for transporting the suctioned volume from a respiratory trauma region;
the extraction tube further comprising a proximate end and a distal end,
the proximate end adapted to engage a suction orifice responsive to reduced pressure in the vacuum body, and
the distal end adapted for fluidic communication with the respiratory trauma region; and
a rake defined by a surface adjacent the distal end, the surface having an area adapted for manual manipulation of viscous or solid material, the rake including an annular surface based on a circumference of the extraction tube, the annular surface increasing a rigidity of the rake surface.

* * * * *